United States Patent [19]
DiCosimo et al.

[11] Patent Number: 4,571,443
[45] Date of Patent: Feb. 18, 1986

[54] PROCESS FOR EFFECTING OXIDATIVE DEHYDRODIMERIZATION

[75] Inventors: Robert DiCosimo, Shaker Heights; James D. Burrington, Richmond Heights; Robert K. Grasselli, Aurora, all of Ohio

[73] Assignee: The Standard Oil Company, Cleveland, Ohio

[21] Appl. No.: 757,984

[22] Filed: Jul. 23, 1985

[51] Int. Cl.$^4$ .............................. C07C 2/72
[52] U.S. Cl. .................... 585/428; 585/435; 585/441; 585/510; 585/601; 422/239
[58] Field of Search ............ 422/239; 585/428, 429, 585/510, 601, 435, 441

[56] References Cited

U.S. PATENT DOCUMENTS

| | | | |
|---|---|---|---|
| 3,361,839 | 1/1968 | Lester | 585/443 |
| 3,375,288 | 3/1968 | de Rosset | 585/443 |
| 3,435,089 | 3/1969 | Moore, Jr. et al. | 585/601 |
| 4,247,727 | 1/1981 | Tremont et al. | 585/428 |
| 4,278,824 | 7/1981 | Tremont et al. | 585/428 |
| 4,278,875 | 7/1981 | Tremont et al. | 585/428 |
| 4,402,915 | 9/1983 | Nishizaki et al. | 422/202 |
| 4,443,641 | 4/1984 | Tremont et al. | 585/428 |
| 4,454,363 | 6/1984 | Teng et al. | 585/428 |
| 4,460,705 | 7/1984 | Terauchi et al. | 585/428 |

*Primary Examiner*—John Doll
*Assistant Examiner*—A. Pal
*Attorney, Agent, or Firm*—Charles S. Lynch; John E. Miller; Larry W. Evans

[57] ABSTRACT

Certain benzylic and allylic compounds are catalytically oxidatively dehydrodimerized wherein the molecular oxygen oxidant is separated from the substrate by a gas impervious catalyst membrane that conducts oxide ions from the surface of the catalyst membrane wall to the opposite surface thereof which is in contact with the substrate.

3 Claims, No Drawings

PROCESS FOR EFFECTING OXIDATIVE DEHYDRODIMERIZATION

This invention relates to a process for effecting the oxidative dehydrodimerization of allylic and benzylic compounds.

It is known to employ bismuth oxide based catalysts to effect the oxidative dehydrodimerization of such compounds as propylene. In such processes a mixture of propylene and an oxygen containing gas are contacted at an elevated temperature with the catalyst to form the dimerization product(s). Since the oxygen is in contact with the hydrocarbon, an undesirable amount of burning of hydrocarbon to carbon oxide occurs. Also, when a dilute oxygen gas (such as air) is employed, large amounts of gas, such as nitrogen and excess oxygen, must be separated from the reaction effluent.

It is an object of the present invention to provide a process for the oxidative dehydrodimerization of allylic and benzylic compounds in the presence of a catalyst containing bismuth wherein the oxidant, molecular oxygen, is maintained out of direct contact with the substrate.

It is another object of the invention to provide such a process wherein oxidant gas components need not be separated from the reaction product dimers.

Other objects, as well as aspects, features and advantages, of the invention will be apparent from a study of the specification, including the specific examples and the claims.

These and other objects are accomplished by the present invention according to which there is provided a process for the catalytic oxidative dehydrodimerization of a substrate compound,

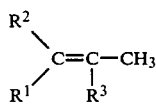

to yield a product,

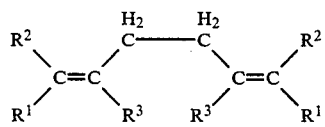

wherein $R^2$ is H, alkyl, phenyl, heteroaromatic containing a single N atom as the sole heteroatom, or cyano, and wherein $R^1$ and $R^3$ either (1) together complete a single ring aromatic group, (2) together with a single N atom complete a single ring heteroaromatic group containing only one heteroatom, or (3) are each independently selected from H, alkyl, phenyl, cyano or a single ring heteroaromatic group having one N atom as the sole heteroatom, with the proviso that when (3) is selected neither $R^1$ nor $R^2$ is bonded to the carbon containing the double bond by a carbon that is bonded to H, and wherein said substrate has 3-12 C atoms, said process comprising:

(A) providing a crystalline, oxide ion conductive, catalyst in the form of a fluid-impervious membrane forming a wall separating a reaction zone and an oxidant supply zone so that fluid cannot flow from either zone to the other, (B) introducing said substrate into said reaction zone in the vapor or gaseous phase in contact with said catalyst, and (C) introducing a gas containing molecular oxygen into said supply zone in contact with said catalyst, the reaction zone and said catalyst being maintained at a temperature above 500° C. at which the catalyst membrane conducts oxide ions across said membrane from the supply zone to the surface of the catalyst membrane forming a wall of the reaction zone, said crystalline, oxide ion conductive, catalyst having the atoms and atomic proportions indicated by the following empirical formula:

$$BiL_aM_bO_x$$

wherein

L is at least one of Y, V, Nb, Ta, W, Mo, Pb, La, Nd, Sm, Er, Yb, Dy and Gd;

M is at least one of Ca, Ba, and Sr;

a=0-1, and b=0-0.1.

In the foregoing process, when a and b are both zero the reaction zone and catalyst are maintained above 730° C. since pure bismuth oxide is not conductive below that temperature.

In the present process, when $R^1$ and $R^3$ are members of a ring there is sometimes formed a coproduct of the following formula:

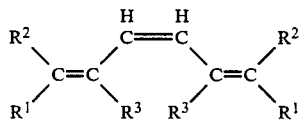

On the other hand, when $R^1$ is H there is sometimes formed some coproduct by cyclization, as follows:

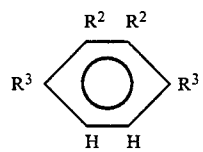

The crystalline, oxide ion conductive, catalysts employed in the present invention as separating catalytic membranes are known compositions. See, for instance the following publications: Harwig et al., *Journal of Solid State Chemistry*, 26. 265-274 (1978); Lawless et al., *Physical Review B*, 28, No. 4, 2125-29, Aug. 15, 1983; Takahashi et al., *Journal of Applied Electrochemistry*, 3, 65-72, 1973; Takahashi et al., *Journal of Applied Electrochemistry*, 5, 197-202, 1975; Verberb et al., *Solid State Ionics*, 3/4, (1981) 463-467, North-Holland Publishing Company; Takahashi et al., *Journal of Applied Electrochemistry*, 5, 187-195, 1975; Suzuki et al., *Solid State Ionics*, 13, (1984) 237-239 North-Holland, Amsterdam; Takahashi et al., *Mat. Res. Bull.*, Vol. 13, pp. 1447-1453, 1978; Kilner et al., *Solid State Ionics*, 5, (1981), 527-530, North-Holland Publishing Company; Takahashi et al., *Journal of Applied Electrochemistry*, 2, (1972), 97-104; Iwahara et al., *Journal of Solid State Chemistry*, 39, 173-180, 1981; Takahashi et al., *J. Electrochem. Soc.*:

Solid-State Science and Technology, 1563-69, Oct. 1977.

In the following exemplary specific examples a catalyst composition was employed which had the empirical formula

was used. It was made as follows:

To a one liter beaker was added 500 mL of 10% $HNO_3$, 300 g (0.62 mol) of $Bi(NO_3)_3.5H_2O$, 47.3 g (0.109 mol) of $La(NO_3)_3.6H_2O$, and a magnetic stirrer bar. The mixture was heated slightly with stirring until all solids had dissolved, then ca. 150 mL of conc. $NH_4OH$ was added dropwise using an additional funnel until the pH of the solution was raised to 4 from an initial value of less than 1, during which time a white precipitate was deposited. The resulting mixture was heated to boiling and the volume of the mixture reduced to ca. 200 mL. The stirrer bar was removed from the beaker, and the mixture heated at 110° C. for 16 h, 290° C. for 4 h and 425° C. for 16 h to yield 157 g of a white solid. The solid was ground to a powder in a mortar and pestle, then heated at 800° C. in air for 16 h and the resulting yellow solid ground to a fine powder and pressed into discs 2-3 mm thick and 13 mm diameter using a hydraulic press. The discs were then again sintered at 800° C. for 16 h.

The disc was seated and sealed between the threaded male and female halves of a cylindrical Inconel® 610 metal (International Nickel Co) chamber, so that the chamber was divided into an upper cylindrical chamber and a lower cylindrical chamber, separated by the wall of the sintered catalyst disc. To insure that the chambers were gas tight and that gas could not leak from one chamber to the other, the assembly was pressure tested at 100 psi. Each half of the reactor contained inlet and outlet ports to which were attached 1/16 inch tubes, so that in practice substrate feed gas was fed into the lower chamber through one tube and port, and reactor effluent out the other port and tube, while air contacted the opposite side of the catalyst disc by being fed into the upper chamber through one tube and port and out the other port and tube. The reactor was heated in a suitcase furnace to the desired reaction temperature.

EXAMPLE 1

A mixture of 20% propylene in helium was passed into the bottom chamber of the reactor at a flow rate of 2.2 mL/min while air was passed through the top chamber of the reactor at 2.2 mL/min. The reactor was heated to 600° C., and the reactor effluent was bubbled through a toluene scrubber cooled to −78° C. The exit gas was collected prior to passage through the scrubber when analyzing for recovered propylene, CO, $CO_2$, $CH_4$, and $C_2$-hydrocarbons by gas chromatography. The scrubber solution was analyzed for hexadienes, cyclohexadienes, and benzene using isooctane as internal standard on a BP-10 capillary gas chromatography column. The reaction was run continuously for 24 h, during which time a 3.2% conversion of propylene was obtained; selectivity to $C_6$ dimers was 77% (53% 1,5-hexadiene, 25% benzene), with 20% $CO_2$, 2% $CH_4$ and 1% CO also being produced.

EXAMPLE 2 (COMPARATIVE)

The reaction in Example 1 was repeated, except that the metal oxide disc was not continuously reoxidized during the reaction; helium was substituted for air and passed through the side of the reactor opposite that of the 20% propylene in helium at a rate of 2.2 mL/min. An initial selectivity to $C_6$ dimers of 80% at 5.2% conversion during the first hour of reaction dropped to 50% selectivity at 2.0% conversion after 4 h; the reaction stopped when the disc became reduced shortly thereafter.

EXAMPLE 3 (COMPARATIVE)

In order to demonstrate the advantage of using the "redox-separated" mode of catalysis over the standard fixed bed approach, 0.20 g of the same catalyst that was used in Example 1 (which was the weight of catalyst in the disc of Example 1, ground to 20-35 mesh was placed between two plugs of glass wool inside a 3 mm ID×21" long quartz tube. The quartz tube was placed inside a suitcase furnace, and a mixture of 20% propylene and 1% oxygen in helium was passed over the catalyst as it was heated to 600° C. The amount of oxygen added to the feed was chosen to produce approximately the same conversion of propylene as was observed in Example 1, so that a comparison of the two reactions could be made. A scrubber containing 5.0 mL of toluene and 50 mL of isooctane as gc internal standard was cooled to −78° C. and placed on the exit of the catalyst containing tube. The gas mixture was fed at a rate of 2.6 mL/min. Analysis for recovered starting material and products was performed as described in Example 1. The selectivity to $C_6$ dimers dropped from 59% selectivity at 4.3% conversion (46%, 1,5-hexadiene and 13% benzene) after 1 h to 32% selectivity to $C_6$ dimers (21% 1,5-hexadiene and 11% benzene) at ca. the same conversion after 2 h, then the selectivity to $C_6$ dimers remained in the range of 32-39% over the next 22 h of operation.

EXAMPLE 4 (COMPARATIVE)

The reaction described in Example 3 was repeated, except that no oxygen was added to the 20% propylene in helium feed. The selectivity to $C_6$ dimers dropped from 74% selectivity at 3.8% conversion (55% 1,5-hexadiene and 19% benzene) to 36% selectivity (benzene only no 1,5-hexadiene) at 0.5% conversion after 6 h. At 7 h conversion of propylene was only 0.3%, with $CO_2$, CO and $CH_4$ the only observed products.

EXAMPLE 5

In this example the substrate was toluene. Helium was fed into the bottom chamber of the reactor at 3.6 mL/min, and toluene and water were added to the carrier gas at a rate of 1.0 mmol/h and 2.0 mmol/h, respectively, by syringe pump. Air was passed through the top chamber of the reactor at the rate of 3.6 mL per min. The reaction was run at 600° C., and a scrubber containing 5.0 mL of dichloromethane cooled to 0° C. was used to collect the reaction products. Nonane and tetradecane were used as g.c. internal standards. At 2.0% conversion, a 50% selectivity to toluene dimers (15% trans-stilbene and 35% bibenzyl) was obtained.

EXAMPLE 6

When a mixture of 20% isobutylene in helium is passed into the lower chamber of the reactor at a flow rate of 2.2 mL/min while air is passed through the upper chamber at the rate of 2.2 mL/min, with the reactor being heated to 600° C., and the lower chamber effluent is recovered as in the first example, p-xylene and 2,5-dimethyl-1,5-hexadiene are products of the reaction.

EXAMPLE 7

The oxidative dehydrodimerization of methacrylonitrile to 2,5-dicyano-1,5-hexadiene and 1,4-dicyanobenzene is carried out in a manner similar to Example 5. Helium carrier gas (3.6 mL/min) to which is added 1 mmol/h of methacrylonitrile by syringe pump is introduced into the lower chamber of the previously described reactor heated to 600° C., while 3.6 mL/min of air is passed through the upper chamber.

EXAMPLE 8

The oxidative dehydrodimerization of α-methylstyrene to p-terphenyl and 2,5-diphenyl-1,5-hexadiene is carried out in a manner similar to Example 5. Helium carrier gas (3.6 mL/min) to which is added 1 mmol/h of α-methylstyrene by syringe pump is introduced into the lower chamber of the previously described reactor heated to 600° C., while 3.6 mL/min of air is passed through the upper chamber.

EXAMPLE 9

The oxidative dehydrodimerization of p-tolunitrile to 1,2-di-(4-cyanophenyl)ethylene and 1,2-di-(4-cyanophenyl)ethane is carried out in a manner similar to Example 5. Helium carrier gas (3.6 mL/min) to which is added 1 mmol/h of p-tolunitrile by syringe pump is introduced into the lower chamber of the previously described reactor heated to 600° C., while 3.6 mL/min of air is passed through the upper chamber.

As will be evident to those skilled in the art various modifications of this invention can be made or followed in the light of the foregoing disclosure and discussion without departing from the spirit and scope of the disclosure or from the scope of the claims.

We claim:

1. A process for the catalytic oxidative dehydrodimerization of a substrate compound,

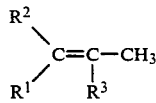

to yield a product,

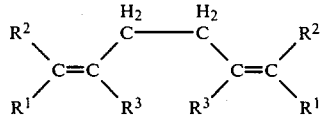

wherein $R^2$ is H, alkyl, phenyl, heteroaromatic containing a single N atom as the sole heteroatom, or cyano, and wherein $R^1$ and $R^3$ either (1) together complete a single ring aromatic group, (2) together with a single N atom complete a single ring heteroaromatic group containing only one heteroatom, or (3) are each independently selected from H, alkyl, phenyl, cyano or a single ring heteroaromatic group having one N atom as the sole heteroatom, with the proviso that when (3) is selected neither $R^1$ nor $R^2$ is bonded to the carbon containing the double bond by a carbon that is bonded to H, and wherein said substrate has 3–12 C atoms, said process comprising:

(A) providing a crystalline, oxide ion conductive, catalyst in the form of a fluid-impervious membrane forming a wall separating a reaction zone and an oxidant supply zone so that fluid cannot flow from either zone to the other, (B) introducing said substrate into said reaction zone in the vapor or gaseous phase in contact with said catalyst, and (C) introducing a gas containing molecular oxygen into said supply zone in contact with said catalyst, the reaction zone and said catalyst being maintained at a temperature above 500° C. at which the catalyst membrane conducts oxide ions across said membrane from the supply zone to the surface of the catalyst membrane forming a wall of the reaction zone, said crystalline, oxide ion conductive, catalyst having the atoms and atomic proportions indicated by the following empirical formula:

$$BiL_aM_bO_x$$

wherein

L is at least one of Y, V, Nb, Ta, W, Mo, Pb, La, Nd, Sm, Er, Yb, Dy and Gd;

M is at least one of Ca, Ba, and Sr;

a=0–1, and b=0–0.1.

2. A process of claim 1 wherein said substrate is propylene and said product is 1,5 hexadiene.

3. A process of claim 1 wherein said substrate is toluene and said product is trans-stilbene.

* * * * *